United States Patent
Li et al.

(10) Patent No.: US 6,571,005 B1
(45) Date of Patent: May 27, 2003

(54) FEATURE EXTRACTION AND NORMALIZATION ALGORITHMS FOR HIGH-DENSITY OLIGONUCLEOTIDE GENE EXPRESSION ARRAY DATA

(75) Inventors: Cheng Li, Los Angeles, CA (US); Wing Hung Wong, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/556,497

(22) Filed: Apr. 21, 2000

(51) Int. Cl.[7] .................................................. G06K 9/00
(52) U.S. Cl. ...................................................... 382/133
(58) Field of Search ................................. 382/128, 133, 382/100; 435/6; 128/922; 356/39; 377/10

(56) References Cited

U.S. PATENT DOCUMENTS

| | | | | |
|---|---|---|---|---|
| 5,790,692 A | * | 8/1998 | Price et al. .................. | 382/133 |
| 6,007,994 A | * | 12/1999 | Ward et al. ..................... | 435/6 |
| 6,027,880 A | * | 2/2000 | Cronin et al. .................. | 435/6 |
| 6,040,138 A | * | 3/2000 | Lockhart et al. ............... | 435/6 |
| 6,124,102 A | * | 9/2000 | Fodor et al. .................. | 435/7.1 |
| 6,156,502 A | * | 12/2000 | Beattie .......................... | 435/6 |
| 6,171,793 B1 | * | 1/2001 | Phillips et al. ................. | 435/6 |
| 6,263,095 B1 | * | 7/2001 | Rushbrooke et al. ....... | 382/128 |

OTHER PUBLICATIONS

Alon, U. et al., "Broad patterns of gene expression revealed by clustering analysis of tumor and normal colon tissues probed by oligonucleotide arrays", *Proc. Natl. Acad. Sci. USA*, vol. 96, pp. 6745–6750 (1999).

Chen, Yidong et al., "Ratio–Based Decisions And The Quantitative Analysis of cDNA Microarray Images", *Journal of Biomedical Optics*, vol. 2 No. 4, 364–374 (1997).

Eisen, Michael B. et al., "Cluster analysis and display of genome–wide expression patterns", *Proc. Natl. Acad. Sci. USA*, vol. 95, pp. 14863–14868 (1998).

Ermolaeva, Olga et al., "Data management and analysis for gene expression arrays", *Nature Genetics*, vol. 20 (1998).

Golub, T.R. et al., "Molecular Classfication of Cancer: Class Discovery and Class Prediction by Gene Expression Monitoring", *Science*, vol. 286 (1999).

Lipshutz, Robert J., et al., "High density synthetic oligonucleotide arrays", *Nature Genetics Supplement*, vol. 21 (1999).

(List continued on next page.)

*Primary Examiner*—Timothy M. Johnson
(74) *Attorney, Agent, or Firm*—Bingham McCutchen LLP; Chris J. Ullsperger (57) ABSTRACT

A characteristic intensity of a feature in image data generated by scanning a microarray probe is determined. A set of pixels of the image data that nominally represent the feature is identified. The pixels each have an value (such as an intensity value) associated therewith. For each of a plurality of subsets of the set of pixels, a variation statistic value is determined that corresponds to a variation in the values associated with the pixels of that subset. One of the subsets of pixels is chosen based on the determined variation statistic values. A method is also described to relate a first expression array of probes to a second expression array of probes. A subset of the probe for the arrays is determined based on a comparison of the ordering of the subset of the probes of the second array, according to a particular characteristic of the probes, to the ordering of corresponding probes in the first array according to the particular characteristic of the probes. A relationship of the second expression array to the first expression array is determined based on the subset of probes o f the second expression array to the corresponding probes of the first array.

5 Claims, 5 Drawing Sheets-

OTHER PUBLICATIONS

Lockhart, David J. et al., "Expression monitoring by hybridization to high–density oligonucleotide arrays", *Nature Biotechnology*, vol. 14, (1996).

Mahadevappa, Mamatha and Warrington, Janet A., "A high–density probe array sample preparation method using 10– to 100–fold fewer cells", *Nature Biotechnology*, vol. 17 (1999).

Schena, Mark et al., "Quantitative Monitoring of Gene Expression Patterns with a Complementary DNA Microarray", *Science*, vol. 270 (1995).

Shalon, Dari et al., "A DNA Microarray System for Analyzing Complex DNA Samples Using Two–color Fluorescent Probe Hybridization", *Genome Research*, 6:639–645 (1996).

Tamayo, Pablo et al., "Interpreting patterns of gene expression with self–organizing maps: Methods and application to hematopoietic differentiation", *Proc. Natl. Acad. Sci. USA*, vol. 96, pp. 2907–2912 (1999).

Wahba, Grace, "Spline Models for Observational Data", *Society for Industrial and Applied Mathematics*, (1990).

Wodicka, Lisa et al., Genome–wide expression monitoring in *Saccharomyces cerevisiae, Nature Biotechnology*, vol. 15 (1997).

Zhu, Hua et al., "Cellular gene expression altered by human cytomegalovirus: Global monitoring with oligonucleotide arrays", *Proc. Natl. Acad. Sci. USA*, vol. 95, pp. 14470–14475, (1998).

* cited by examiner

FEATURE EXTRACTION AND NORMALIZATION ALGORITHMS FOR HIGH-DENSITY OLIGONUCLEOTIDE GENE EXPRESSION ARRAY DATA

GOVERNMENT CONTRACT STATEMENT

At least some of the subject matter of this disclosure was developed while under contract with the National Science Foundation (grants DMS-9703918 and DBI-9904701).

TECHNICAL FIELD

The invention relates to the analysis of gene probe microarrays and, in particular, to the analysis of image data produced by such gene probe microarrays.

BACKGROUND

Monitoring gene expression using high-density microarrays is a technique in the study of cell functions and the associated biochemical pathways, candidate gene identification, cellular response to drug compounds, and classification of disease states. For example, see:

Alon, U. et al. Broad patterns of gene expression revealed by clustering analysis of tumor and normal colon tissues by oligonucleotide arrays. *Proc. Natl. Acad. Sci. USA*, 96, 6745–6750 (1999).

Zhu, H. et al. Cellular gene expression altered by human cytomegalovirus: global monitoring with oligonucleotide arrays. Proc. Natl. Acad. Sci. USA 95, 14470–14475 (1998).

Wodicka, L. et al. Genome-wide expression monitoring in Saccharomyces cerevisiae. Nature Biotechnology 15, 1359–1366 (1997).

Eisen, M. B. et al. Cluster analysis and display of genome-wide expression patterns. Proc. Natl. Acad. Sci.USA 95, 14863–14868 (1998).

Tamayo, P., et al. Interpreting patterns of gene expression with self-organizing maps: Methods and application to hematopoietic differentiation. Proc. Natl. Acad. Sci. USA 96, 2907–2912 (1999).

Golub, T. R. et al. Molecular classification of cancer Class discovery and class prediction by gene expression monitoring. Science 286, 531–537 (1999).

It appears that recent research has largely focused on enhancing the microarray technology itself and the corresponding experimental protocols. For example, see Lockhart, D. J. et al. Expression monitoring by hybridization to high-density oligonucleotide arrays. *Nature Biotechnology* 14, 1675–1680 (1996).

Schena, M. et al. Quantitative monitoring of gene expression patterns with a complementary DNA microarray. *Science* 270, 467–470 (1995).

Shalon, D. et al. A DNA microarray system for analyzing complex DNA samples using two-color fluorescent probe hybridization. *Genome Research* 6, 639–645 (1996).

Mahadevappa, M. & Wodicka, L. A high-density probe array sample preparation method using 10- to 100-fold fewer cells. *Nature Biotechnology* 17, 1134–1136 (1999).

Other research has focused on developing higher-level analysis methods such as clustering and classification. For example, see Chen, Y. et al. Ratio-based decisions and the quantitative analysis of cDNA microarray images. Journal of Biomedical Optics 2, 364–374 (1997).

Chen et al. detailed algorithms for image segmentation and confidence intervals for expression ratios for cDNA microarray data.

The fundamentals of oligonucleotide expression array technology are described, for example, in the Lockhart paper cited above and are well-known in the art. The oligonucleotide expression array technology is broadly discussed here to provide a frame of reference for discussion of the invention. In particular, genes are represented on a probe array by some number of sequences of a particular length that uniquely identify the genes and that ostensibly have optimal hybridization characteristics. Each oligonucleotide (probe) is synthesized in a small cell that contains a large number (typically between $10^6$ and $10^7$) of copies of a given probe.

A mismatch (MM) oligonucleotide is designed to correspond to a perfect match (PM) oligonucleotide pulled from a gene sequence. In an MM oligonucleotide, typically the center base position of the oligonucleotide has been mutated. The MM probes give some estimate of the random hybridization and cross hybridization signals.

To use an oligonucleotide array, RNA samples are prepared and fluorescently labeled according to a particular protocol (e.g., the protocol set forth by Lockhart et al. in the article cited above), and then the labeled RNA sample is hybridized to the corresponding probes on the array. The array then goes through an automated staining/washing process (e.g., using an Affymetrix fluidics station), and the array is scanned using a confocal laser. The scanner generates an image of the array by exciting each cell with its laser, detects the resulting photon emissions from the fluorescently labeled RNA that has hybridized to the probes in the cell, and then converts the detected photon emissions into a raw intensity value for each cell. "Features" (comprised of groups of cells) are "extracted" based on the images, and characteristic feature intensities are computed from the raw cell intensities. It can be determined from the features' "characteristic intensity" whether a particular gene is present in the array, and the quantity at which the gene is present.

Conventional feature extraction is now discussed in greater detail. For example, as discussed by Wodicka et al.(1997), the raw oligonucleotide array image has recognizable patterns at each corner that allows the determination of the positions of the corners of the array. The number of features in each row and column is known. Once the corners are determined, the positions of each feature in the array are computed.

Figure 1A:
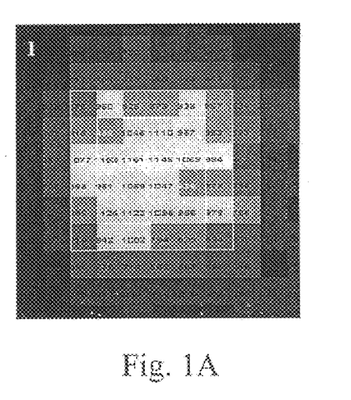

As can be seen from FIG. 1A, the boundary pixels of a feature are typically distorted by blurring (i.e. their levels are "pulled" towards the level of a neighboring feature) and do not faithfully represent the true intensity of the feature. Therefore, the boundary pixels are conventionally removed before the characteristic feature intensity is computed. That is, the intensities of the boundary pixels of a feature are not considered in determining a characteristic intensity value for the feature. In most cases, after removing the boundary pixels from a feature, the feature is represented by a 6×6 block of pixels that remain.

Then, the characteristic intensity for the feature is determined, for example, by computing an average intensity of the remaining pixels. It can be seen from FIG. 1A that determining the median of the remaining 6×6 pixels often results in determining the median value from a more variable region than, say, the most homogenous block of pixels (e.g., a 4×4 pixel block) within the 6×6 pixel block. This can result in a downward bias from the "true" characteristic feature intensity.

Figure 1B:
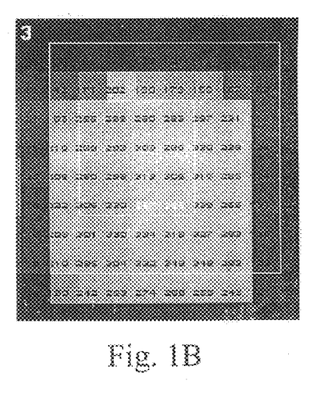
FIG. 1B illustrates how grid mismatch contributes to inadequate feature extraction.

Furthermore, FIG. 1B illustrates how a misalignment of the basic grid can result in a failure to extract the central part of the true feature.

What is desired is a feature extraction method that more robustly and reliably extracts the "useful" portion of a true feature for determining characteristic feature intensity.

Furthermore, it is well known that the comparison of gene expression results across experiments is enhanced when the results of the experiments are normalized to a single scale. Normalizing multiple probe arrays to allow direct array-to-array comparisons has presented a great challenge. Conventional normalization methods include 1) linear normalization and nonlinear regression, and 2) methods using housekeeping genes or staggered spike-in controls.

With linear normalization, it is assumed that the intensities between two or more arrays are related as a straight line with a zero y-intercept. Its use leads to multiplication by a scaling factor (slope of the line) to make the mean of the "experiment" chip the same as that of the baseline chip. A description of this technique applied to Affymetrix probe arrays is given by Alon et al. (1999). For example, see page 6746, lines 2–4 which states that "To compensate for possible variations between arrays, the intensity of each EST on an array was divided by the mean intensities of all ESTs on that array and multiplied by a nominal average intensity of 50."

Ignoring the slight differences of the number of retained probe pairs per gene (due to outlier probe removal), the essential effect of these operations is equivalent to the multiplication of each probe pair difference by a constant scaling factor.

Figure 2:
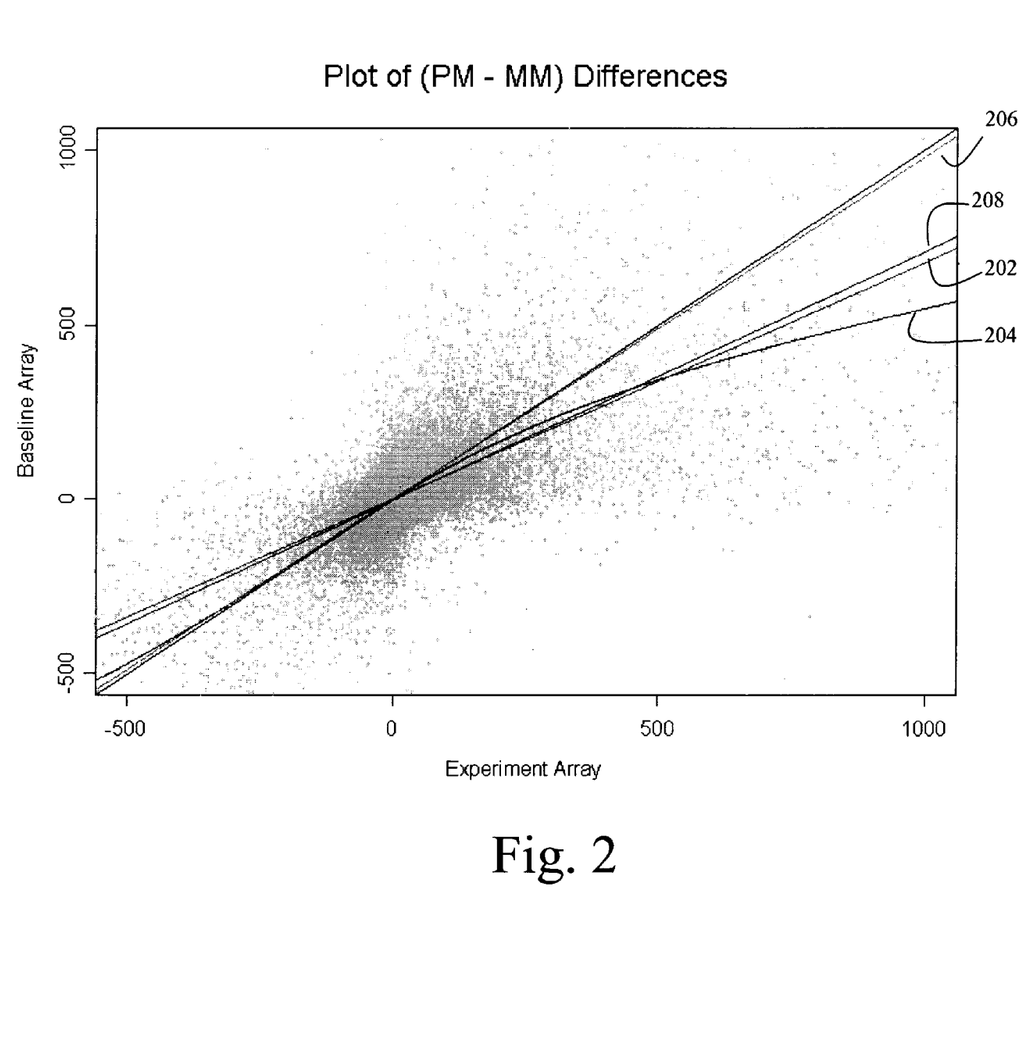
FIG. 2 is a scatter plot with the PM-MM slope superimposed thereon, illustrating the drawbacks of conventional normalization techniques.

Chen et al. (1998) describe an application of the linear normalization technique to cDNA spotted arrays, where one intensity channel is normalized against another on the same array. For example, on page 371, formulae (12) & (13) represent a linear scaling operation across the whole array. (The Chen paper actually used a more complicated procedure where the scaling is applied iteratively in connection with the fitting of the density for the ratios.) Although the linear normalization technique is simple and robust, this method has the drawback that it does not account well for nonlinear relations. For example, FIG. 2 illustrates a situation where the slope in the low intensity region (of the scatter plot of PM/MM differences between two arrays) is substantially different from the slope in the high intensity region. In fact, a 10%–50% difference in slope values between regions is quite common. A non-linear regression technique (e.g., generalized cross-validation or GCVSS as described in Wahba, G. *Spline Methods for Observational Data*. CBMS-NSF regional conference series in applied mathematics. Philadelphia: SIAM (1990)) may be employed, but even non-linear regression can be inadequate if the expression profiles of the various arrays vary greatly from each other.

The drawbacks of the conventional normalization methods can be seen with reference to FIG. 2. Specifically the PM/MM difference from two murine Affymetrix Mu6500SubA probe array experiments are plotted in FIG. 2. The line 202 is the line generated by the LR normalization method, the curve 204 is generated by the GCVSS method, and the lines 206 and 208 are generated by applying the LR method to low and high differences, respectively (the low/high cutoff was determined empirically from the GCVSS line 204 matches the line 206 at the low end and the 208 and 202 lines at the high end, although the data between the two experiments is not really linearly related.

It has also been suggested (e.g., see Ermolaeva et al; 1998) that normalization between arrays can be based on a set of "housekeeping" genes. Unfortunately, many of the genes conventionally used as housekeeping genes (e.g., 8 actin, glyceraldehyde-3-phosphate dehydrogenase, transferrin receptor, signal transducer and activator of transcription 1, among others) have ranges of differential expression similar to other genes whose differential expression patterns are deemed biologically relevant to the system under study. In accordance with one known method, control cRNAs for bacterial and phage genes (e.g., BioB, BioC, BioD, and cre) are consistently added to hybridization mixtures at known concentrations. However, these controls are often prepared in bulk and completely independently of the sample being profiled, and so, the normalization relation between the controls on different arrays typically does not reflect the true normalization relation for the biologically relevant genes of interest.

What is desired is a normalization method that more accurately reflects the true normalization relation.

SUMMARY

In accordance with one aspect of the invention, a method is provided to determine a characteristic intensity of a feature in image data generated by scanning a microarray probe. A set of pixels of the image data that nominally represent the feature is identified. The pixels each have an value (such as an intensity value) associated therewith. For each of a plurality of subsets of the set of pixels, a variation statistic value is determined that corresponds to a variation in the values associated with the pixels of that subset. One of the subsets of pixels is chosen based on the determined variation statistic values.

In accordance with a further aspect of the invention, a method is provided to relate a first expression array of probes to a second expression array of probes. A subset of the probe for the arrays is determined based on a comparison of the ordering of the subset of the probes of the second array, according to a particular characteristic of the probes, to the ordering of corresponding probes in the first array according to the particular characteristic of the probes. A relationship of the second expression array to the first expression array is determined based on the subset of probes of the second expression array to the corresponding probes of the first array.

BRIEF DESCRIPTION OF FIGURES

FIG. 1A illustrates how boundary pixels "blur" a feature, while

DETAILED DESCRIPTION

What is now described, broadly speaking, is a method for analyzing raw data generated by gene expression microarrays, including oligonucleotide expression microarrays. Such an array may include the microarray known as the GeneChip® probe array provided by Affymetrix of Santa Clara, Calif. Steps of feature extraction and normalization are particularly described.

Feature Extraction

Figure 3:
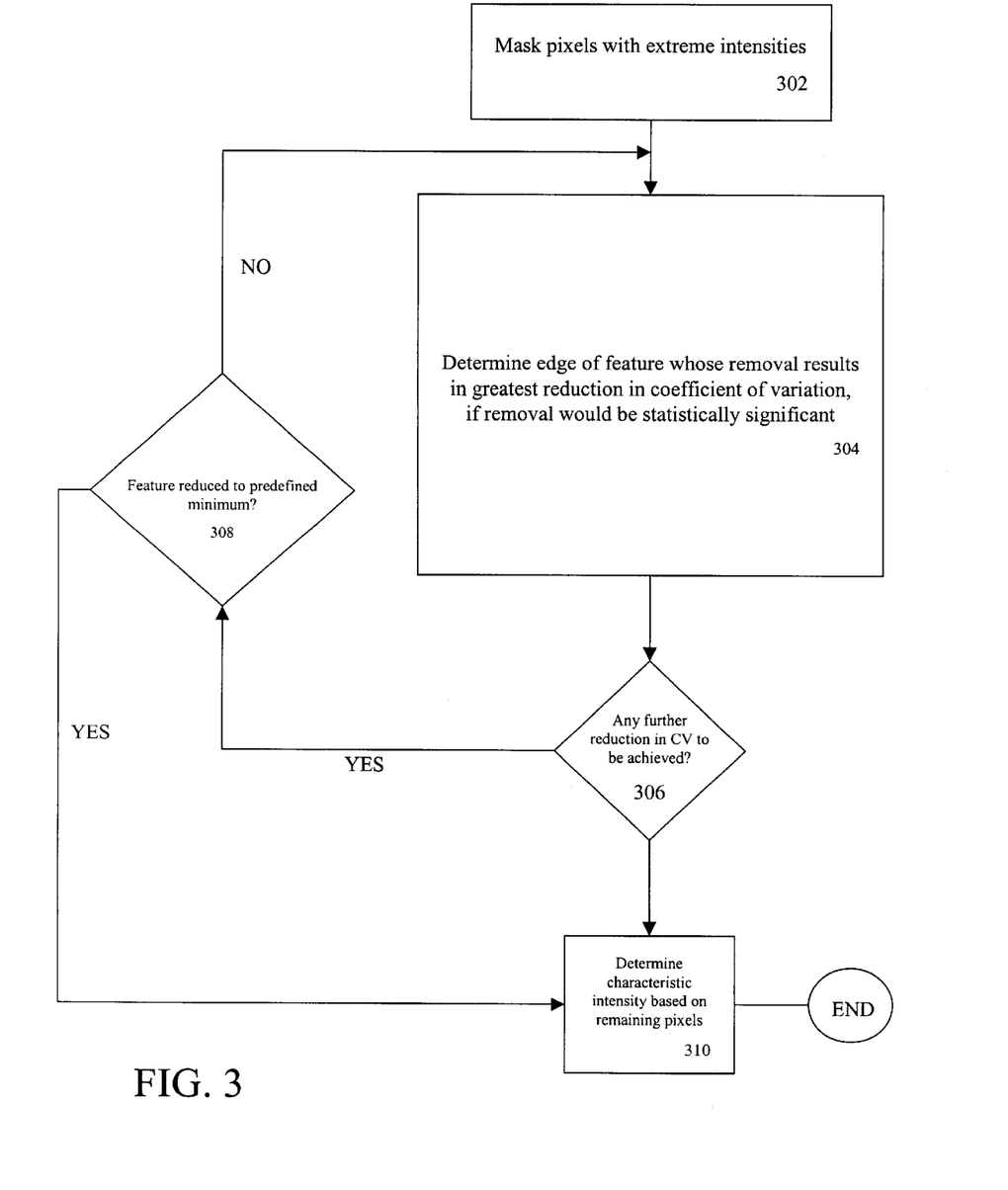
FIG. 3 is a flow chart illustrating an embodiment of an adaptive pixel selection (APS) method in accordance with the invention.

Now, an adaptive pixel selection (APS) method for feature extraction is described with reference to FIG. 3. The APS method is carried out on a set of pixels at least nominally on pixels preliminarily identified as being part of a feature. At step 302, the pixels with extreme intensities are masked. (For example, pixels more than three standard deviations from the mean pixel value within a feature, including the boundary pixels of the feature, are removed.) At step 304, it is determined which edge of the feature, if its pixels are removed, would result in the greatest reduction in the coefficient of variation (CV) of the remaining pixels. Preferably the pixels of the edge are removed only if the reduction in CV is statistically significant.

At step 306, it is determined if any further reductions in CV can be achieved by removing another edge. If so, it is determined at step 308 if the feature is already reduced to a predetermined minimum number of pixels. If no further reduction in CV can be achieved or if the feature is already reduced to the predetermined number of pixels, then at step 310 the characteristic intensity of the feature is determined from the remaining pixels (e.g., by taking a mean of the raw intensity values for the remaining pixels). Otherwise, steps 304, 306 and 308 are repeated.

In some embodiments, the pixel selection process just described is constrained by forcing adjacent subregions selected by the process (corresponding to adjacent features) to be separated by at least two pixels. It is thought that forcing such a separation tends to select the most homogenous group of pixels whose mean value is used to represent the intensity for the given feature.

In another embodiment, rather than "shrinking" the set of pixels under consideration, the set of pixels under consideration is instead "grown" from a seed pixel (or set of pixels) until a subset of pixels corresponding to the feature is achieved that has an appropriately minimal CV. In this case, "appropriately minimal" may be the subset of pixels that has the absolute minimum CV. For example, in accordance with one such "growing" embodiment, the central 2×2 pixel block of the nominal feature pixels is selected as the seed region. Then, either a row or column is added to the already-selected region. Typically, the row or column is chosen that, when added, results in the smallest increase in variability of pixel intensity of the selected region. The growing step is iteratively repeated until a predetermined size is achieved (e.g., 4×4 pixels or 5×5 pixels). In addition, in some embodiments, the adding step is constrained such that the resulting enhanced region does not deviate too drastically from a particular shape (typically square).

In an experiment, the APS "shrinking" method was compared to the median method, by examining twelve replicate oligonucleotide arrays. Replicate data were generated by hybridizing the same cRNA hybridization cocktail onto six high-density Affymetrix Hu6800 probe arrays and six "A" probe arrays from the low-density Affymetrix Hu6800 four-chip set. The twelve arrays were normalized using the IDS/GCVSS normalization method described below. It is reasonable to expect, after normalization, the intensities for any given feature across the twelve replicates to be roughly equal, since the same sample was hybridized onto each array. For each feature across the twelve replicate arrays, the feature-intensity standard deviations (SD) were computed after using the median and the APS methods to determine the feature intensities.

A "good" feature extraction algorithm would lead to a small SD among the replicates. For these arrays, 74% of the APS feature-intensity SDs were smaller than the corresponding median feature-intensity SDs and, in these cases, the average ratio between the median-computed SD to the APS-computed SD was 2.10. On the other hand, the average ratio between the APS-computed SDs and the median-computed SDs was only 1.27, when the APS-computed SD was larger than the median-computed SD. Thus the APS algorithm leads to a 40% reduction in the intensity standard deviation across replicate arrays, when compared to the median algorithm.

Given that these feature intensity calculations form the basis for all future analyses, any method that significantly reduces the measurement error will serve to increase the sensitivity and specificity of the experiment.

Normalization

Now, normalization is described with reference to FIGS. 4 and 5. The normalization is carried out by a so-called "invariant difference selection" method (IDS). Broadly speaking, the IDS method chooses a subset of some features of an array for normalization based on differences between some characteristic of those features. For example, the feature intensities or the PM/MM intensity differences may serve as the basis for fitting a normalization relation.

Using the PM/MM differences as an illustrative example, a set of probes are said to be invariant if the ordering of these probes according to the PM/MM differences in the experiment array, is the same as that in the baseline array. Intuitively, if a gene is truly differentially expressed, then the PM/MM differences for this gene are more likely to have different ranks relative to the other probes, and hence they are not likely to be included in a large invariant set. In some embodiments, the maximal invariant set is computed using a dynamic programming algorithm. However the resulting set is typically too small to form a reliable normalization curve. In another embodiment, the IDS method finds an approximately invariant set of differences that is not necessary maximal, but is large enough for reliable fitting of the normalization relation.

Figure 4:
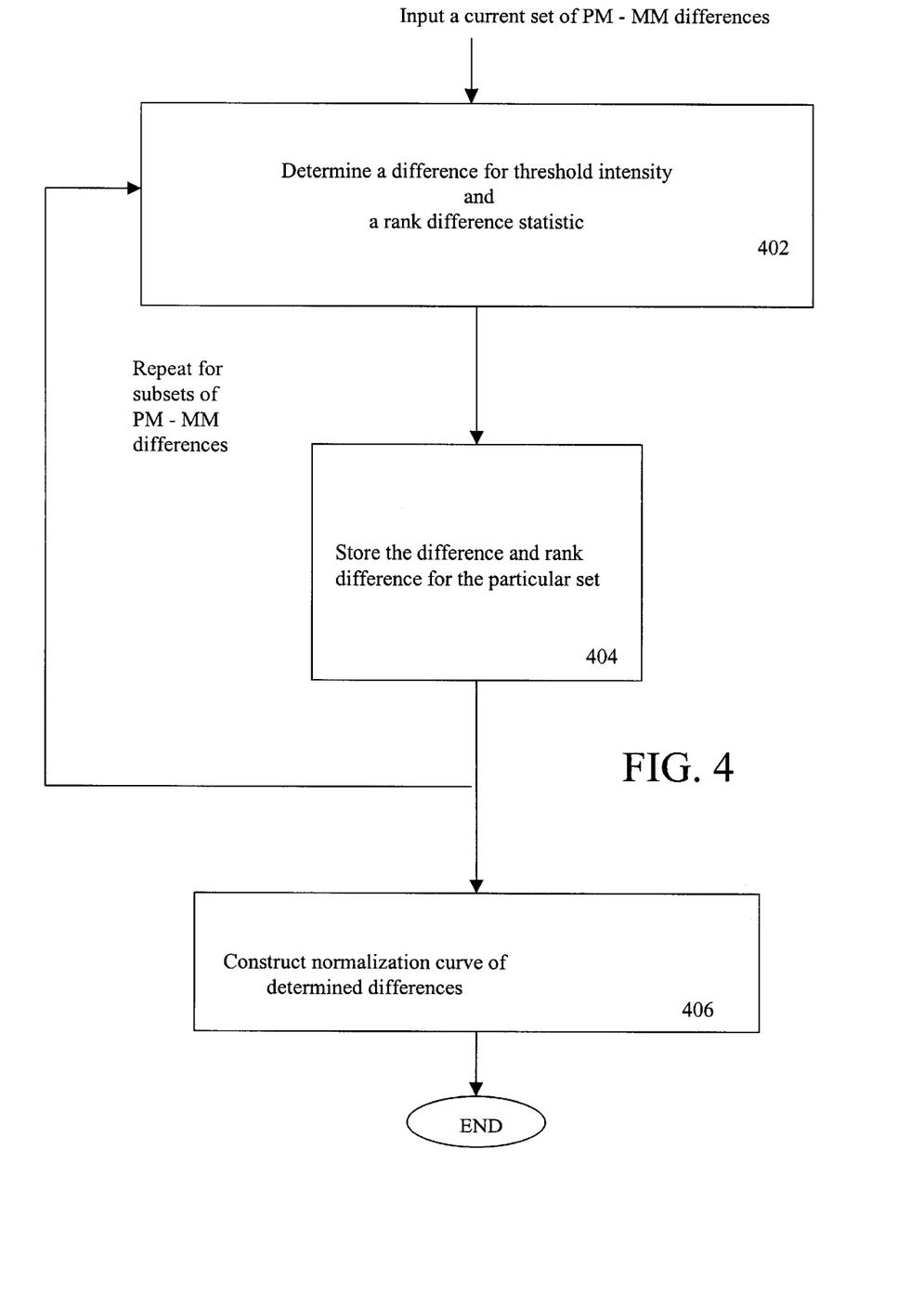
FIG. 4 is a flow chart illustrating an embodiment of an invariant difference selection (IDS) method, particularly with the invention and useful in normalizing results between various microarrays.
Figure 5:
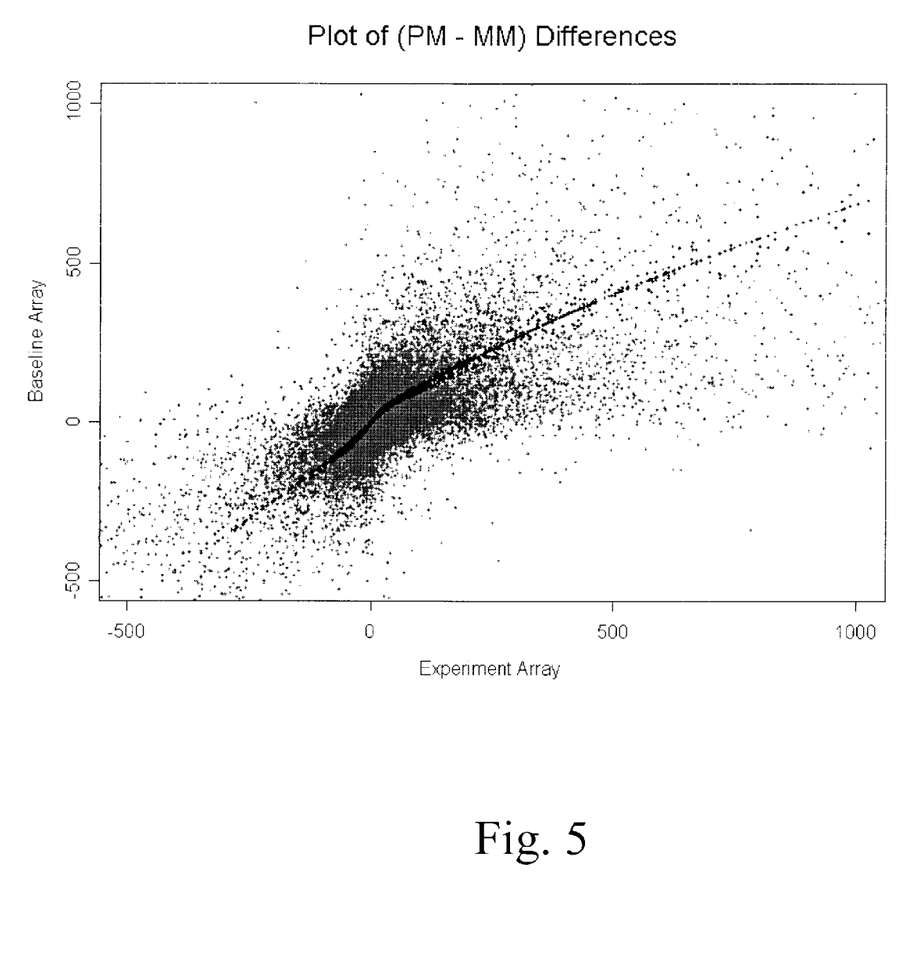
FIG. 5 is a scatter plot of PM-MM differences with IDS/GCVSS normalization curve superimposed thereon, the differences for normalization were selected in accordance with an embodiment of the invention.

Turning now to FIG. 4, in accordance with one embodiment, various subsets of the PM-MM difference values are input to a difference calculation. That is, at step 402, the following expressions are evaluated for the input differences:

$$R_i = [L(B_i + E_i) + H(2N - B_i - E_i)]/2N$$

$$D_i = 2|B_i - E_i|/(B_i + E_i)$$

where L and H are the rank difference thresholds for the low and high ends of the difference intensity range, $B_i$ and $E_i$ are the ranks for the $i^{th}$ difference of the baseline and experiment arrays, and N is the total number of differences that were ordered in the current iteration of the method. $R_i$ defines the threshold for difference intensity i by linearly interpolating the threshold between a low difference intensity threshold, given by L, and a high difference intensity threshold, given by H.

The interpolation addresses the property that there are many more points at low intensities than at high intensities. While a more strict threshold policy can practically be enforced at the low end, it is more practical to relax the threshold constraint at the high end such that enough points are obtained in this range to reliably establish the normalization relation. $D_i$ is the rank difference test statistic used to determine if the it difference should be included in the invariant set, for the current iteration of the algorithm. The $i^{th}$ difference is considered approximately invariant if $D_i < R_i$.

At step 404, the difference value and rank difference is stored for the particular input set. The selection process then repeats at steps 402 and 404, taking the current set of approximately invariant differences as input, until all differences meet the threshold criteria.

At step 406, the approximately invariant set of differences has been selected and the normalization curve is constructed (e.g., by applying the GCVSS technique described in Wahba 1990 to the invariant set). An example of such a normalization curve is shown in FIG. 5. FIG. 5 shows the same data presented in FIG. 2. The black points represent the differences determined by the IDS technique, and the line is the GCVSS fit of the invariant differences between the baseline and the experiment arrays.

The efficacy of the just-described IDS/GVCSS is now discussed. In comparing the IDS/GCVSS normalization technique to the linear regression (LR) and standalone GCVSS methods, criteria that could be established to test the superiority of one normalization method over another are: 1) the method minimizes the PM/MM intensity difference variances across a series of replicate arrays, and 2) the method preserves expression ratios in simulated data. The first criterion addresses the desire that genes known to have identical expression levels have observed levels as close to identical as possible. The second criterion addresses the desire that criterion 1 not be achieved at the expense of destroying the very biological variation the technology aims to detect.

Table 1 presents the results of comparing the IDS/GCVSS method against the GCVSS method and the LR method, carried out on the same set of twelve replicate probe arrays discussed above. In particular, Table 1 shows results of comparing average difference intensities across a series of twelve replicate probe arrays using no normalization (UN), linear normalization (LR), smoothing spline normalization (GCVSS) and the invariant difference selection/smoothing spline (IDS/GCVSS) methods described in the text. The first number in each value pair of Table 1 represents the percentage of standard deviations, computed across the twelve replicates for each of the genes, that were larger when the normalization technique listed in the leftmost column was compared against the normalization technique listed along the top row. For instance, in cell (LR, IDS) the value pair (0.65, 1.5) indicates that 65% of the difference standard deviations were larger when LR normalization was used compared to the difference standard deviations when the IDS method was used, and of those that were larger, the median LR/IDS ratio of standard deviations was 1.5, i.e., for 65% of the genes, half of those had an LR standard deviation that was more than 1.5 times larger than the corresponding IDS standard deviations.

The results shown in Table 1 indicate that the IDS/GCVSS method is reasonably similar to the standalone GVCSS method, and both are better at making the average of the PM/MM differences for a particular gene, i.e., the average difference intensities, across these replicate arrays more consistent than doing nothing at all or than using the LR method.

TABLE 1

| >Relation | UN | LR | GCVSS | IDS |
|---|---|---|---|---|
| UN | N/A | (0.96, 1.2) | (0.85, 1.7) | (0.74, 1.8) |
| LR | (0.04, 1.0) | N/A | (0.76, 1.4) | (0.65, 1.5) |
| GCVSS | (0.15, 1.3) | (0.24, 1.2) | N/A | (0.46, 1.4) |
| IDS | (0.26, 1.2) | (0.35, 1.3) | (0.54, 1.5) | N/A |

Results from two sets of simulated expression-ratio data are presented in Table 2. In the first set, 300 genes that were consistently detected as present across the 6 low-density replicate probe arrays and 600 from the high-density replicate probe arrays were randomly selected; 6 sets containing 50 genes each for the low-density arrays and 100 genes each for the high-density arrays were then generated by randomly selecting, without replacement, from the sets of 300 and 600 randomly selected genes. The PM/MM differences comprising each of the genes in each of the sets were then multiplied by 2.0, 0.5, 4.0, 0.25, 6.0, and 0.17, respectively, to simulate fold changes between samples. The twelve original replicate probe arrays as well as the twelve modified replicate probe arrays were then normalized using the normalization techniques listed in Table 1.

TABLE 2

| >Relation | LR.1/LR.2 | GCVSS.1/GCVSS.2 | IDS.1/IDS.2 |
|---|---|---|---|
| LR.1/LR.2 | N/A | (0.08, 1.2)/(0.15, 1.3) | (0.94, 9.3)/(0.61, 2.1) |
| GCVSS.1/GCVSS.2 | (0.92, 3.2)/(0.85, 3.2) | N/A | (0.99, 16.5)/(0.95, 3.9) |
| IDS.1/IDS.2 | (0.06, 1.4)/(0.39, 1.4) | (0.01, 1.1)/(0.05, 1.3) | N/A |

The same procedure was applied to the second set, except that 320 genes from the low density arrays and 640 genes from the high-density arrays were randomly selected, and then 16 sets of 20 genes/40 genes each were formed and the corresponding difference intensities were multiplied by 2.0, 0.5, 2.5, 0.4, 3.0, 0.33, 3.75, 0.27, 4.0, 0.25, 5.0, 0.20, 6.0, 0.17, 7.0 and 0.14, respectively, yielding a very diverse differential expression pattern in which as many as 18% of the genes on the arrays were forced to be differentially expressed. The standard deviations of the differences between the true fold change and the observed fold change after normalization were computed for each of the modified genes.

In table 2, the first value in each value pair represents the percentage of standard deviations that were larger when the normalization technique listed in the leftmost column was compared against the normalization technique listed along the top row. For instance, the first value pair (0.94, 9.3) in cell (LR.1/LR.2, IDS.1/IDS.2) indicates that for the first set of data 94 percent of the LR.1 computed standard deviations were larger than the IDS.1 computed standard deviations, and that of those that were larger, the median LR.1/IDS.1 ratio of standard deviations was 9.3, i.e., half of the time, the LR.1 standard deviation is more than 9.3 times larger than the IDS.1 standard deviation.

Table 2, shows that the GCVSS technique makes the average difference intensities more consistent by destroying the very biological variation the technology aims to detect. That is, Table 2 shows how the GCVSS technique is too sensitive to the relatively small number of genes that change. On the other hand, the IDS/GCVSS technique continues to perform better than the other techniques, not only by minimizing the average difference intensity variation across replicates, but also by minimizing the deviation from the true fold change values in the simulated data.

As mentioned above in the introduction to this "Normalization" section, feature intensities may be used for normalization, too. Thus, finally, in another embodiment, normalization is performed on feature intensities rather than PM-MM differences. The method is the same as in the IDS/GCVSS method described above, except that the scatter plot of corresponding differences between the two arrays is replaced by the scatter plot of the corresponding feature intensity values between the two arrays.

Conclusion

Processes for feature extraction and normalization have been described. Because many important decisions as to whether a gene should be pursued as a candidate for a particular biological system under study are directly based on determined expression ratios as well as on the determined differential expression calls, processes that provide for more accurate estimates of these derived statistics can be valuable to users of oligonucleotide array technology.

It should be noted that the image processing techniques may have broader application beyond oligonucleotide arrays or even to microarrays, and claim to such broader application is not intended to be foreclosed by this disclosure.

What is claimed is:

1. A method of relating a first expression array of probes to a second expression array of the same probes, comprising:
    ranking the probes in the first expression array according to a measureable characteristic; and
    ranking the probes in the second expression array according to said measureable characteristic; and
    determining an approximately invariant subset of probes whereby said approximately invariant subset consists of probes for which said ranking by said characteristic in the second expression array is substantially the same as the ranking by said characteristic of corresponding probes in said first expression array; and
    determining the relationship between the first expression array and the second expression array from the values of said characteristics of probes in the approximately invariant subset; and
    wherein the approximately invariant subset is selected from a plurally of subsets of the second array by comparing a first subset of ranked probes of the second array to a corresponding subset of ranked probes of the first array; and
    if the comparison does not meet a particular criterion, the comparing step is repeated in an iterated fashion with a second of the plurality of subsets of probes of the second array, wherein said second subset is a subset of said first subset; and wherein the approximately invariant subset is the subset of the probes for which the comparison meets the particular criterion,
    wherein said second subset consists of probes selected from said first subset which satisfy the requirement that $D_i < R_i$, wherein $$R_i = [L(B_i + E_i) + H(2N - B_i - E_i)]/2N;$$

and wherein $$D_i = 2|B_i - E_i|/(B_i + E_i);$$

wherein i refers to the identity of a given probe; and [0axb]p2wherein L and H are rank difference thresholds for the low and high ands, respectively, of the range of values of said measurable characteristic; and wherein $B_i$ and $E_i$ are the ranks by characteristic value of probe i from said first and second expression arrays, respectively, and
    wherein N is the total number of comparisons of corresponding orders probes in the current iteration;
    and wherein said particular criterion is met when every probe in said first subset satisfies the requirement that $D_i < R_i$.

2. The method of claim 1, wherein said measurable characteristic is the PM/MM intensity difference of array probes.

3. The method of claim 1, wherein said measureable characteristic is the feature intensity of array probes.

4. The method of claim 2 or 3, wherein a nonlinear regression technique is applied to the approximately invariant probe set to determine the relationship between the arrays.

5. The method of claim 4, wherein the step of applying a nonlinear regression technique includes applying a generalized cross-validation step to the approximately invariant probe set.

* * * * *

UNITED STATES PATENT AND TRADEMARK OFFICE
CERTIFICATE OF CORRECTION

PATENT NO. : 6,571,005 B1
DATED : May 27, 2003
INVENTOR(S) : Cheng Li and Wing Hung Wong It is certified that error appears in the above-identified patent and that said Letters Patent is hereby corrected as shown below:

<u>Title page,</u>
Item [57], ABSTRACT,
Line 10, change "o f" to -- of --

<u>Column 6,</u>
Line 65, please change "if the it difference" to -- if the $i^{th}$ difference --;

<u>Column 9,</u>
Line 33, please change "plurally" to -- plurality --;

<u>Column 10,</u>
Line 15, please delete "[0axb]p2";
Line 16, please change "ands" to -- ends --;
Line 23, please change "orders" to -- ordered --.

Signed and Sealed this

Thirtieth Day of September, 2003

JAMES E. ROGAN
*Director of the United States Patent and Trademark Office*